United States Patent [19]

Modrovich

[11] 4,153,511
[45] May 8, 1979

[54] STABILIZED LIQUID COENZYME COMPOSITIONS

[76] Inventor: Ivan E. Modrovich, 591 Beverly Dr., Camarillo, Calif. 93010

[21] Appl. No.: 764,826

[22] Filed: Feb. 2, 1977

Related U.S. Application Data

[63] Continuation of Ser. No. 667,857, Mar. 17, 1976, abandoned.

[51] Int. Cl.$^2$ .............................................. G01N 31/14
[52] U.S. Cl. ....................................... 195/99; 195/63; 195/68; 195/103.5 R
[58] Field of Search .................. 195/99, 101, 103.5 R, 195/63, 68; 536/28; 23/230 B

[56] References Cited

U.S. PATENT DOCUMENTS

| 2,882,244 | 4/1959 | Milton | 252/455 Z |
| 3,819,487 | 6/1974 | Bernt et al. | 195/99 |

FOREIGN PATENT DOCUMENTS 2615958  12/1976  Fed. Rep. of Germany.

OTHER PUBLICATIONS

George et al., Biochim. Biophys. Acta, 191 (1969) pp. 466–468.

Primary Examiner—David M. Naff
Attorney, Agent, or Firm—Romney, Schaap, Golant, Scillieri, Disner & Ashen

[57] ABSTRACT

Labile coenzymes, such as reduced nicotinamide-adenine dinucleotide (NADH$_2$), are stabilized by forming a composition of the coenzyme with an organic solvent such as 1,2 propanediol in the presence of at least 1% by volume of a solid, inert hygroscopic agent such as 10% by volume of a molecular sieve material. The stabilized composition contains less than 0.5% water, shows excellent shelf life and a container in which the composition is stored may be repeatedly opened for use without degradation of the labile coenzyme such as the labile NADH$_2$.

43 Claims, No Drawings

STABILIZED LIQUID COENZYME COMPOSITIONS

RELATED APPLICATION

This application is a continuation of Application Serial No. 667,857, filed Mar. 17, 1976, now abandoned, for STABILIZED LIQUID COENZYME COMPOSITIONS.

BACKGROUND OF THE INVENTION

1. Field of the Invention

This invention relates to the stabilization of labile coenzymes in liquid media.

2. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement stems from the fact that the exact nature of enzymes, as well as the mechanisms of their action, remain unknown for the most part. At present, the greatest limitation on the enzyme reagent manufacturer, by far, lies in the unstable characteristics of his products. Current methodologies require the use of numerous labile ingredients, and these ingredients are more likely to increase, rather than decrease, in number.

The present commercial state of the art used for stabilizing the reactive ability of enzymes or coenzymes is by locking them into a solid matrix either by freeze drying, dry blending such as used for tableting dried powders, primarily in the pharmaceutical diagnostic and related industries and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried control sera (reference serum) list the acceptable bottle to bottle variation of enzyme constituents at ±10% of the mean.

In the clinical diagnostic field the commercial application is represented by, but not limited to, the diagnostic reagents used to determine and quantitate the following constituents in biological fluids:

1. Glutamic-oxalacetic transaminase (SGOT);
2. Glutamic-pyruvic transaminase (SGPT);
3. Lactic dehydrogenase (LDH);
4. Creatine Phosphokinase (CPK);
5. α-Hydroxybuteric dehydrogenase (α-HBD)
6. Glucose (via Hexokinase-G-6-PDH). These reagents react similarily, contain some common labile ingredients, and some of the chemical reactions involved are common. The following chemical reaction scheme is presented as a model to illustrate the general nature of the reactions involved:

REACTION SCHEME 1. — GENERAL MODEL $$\text{SUBSTRATE(S)} \xrightleftharpoons[\text{pH}]{\text{Enzyme 1}} \text{PRODUCT(S)} \quad (1.)$$

$$\text{PRODUCT/SUBSTRATE} + \text{NAD} - \text{NADH}_2 \xrightleftharpoons[\text{pH}]{\text{Enzyme 2}} \text{NADH}_2 - \text{NAD} + \text{PRODUCT} \quad (2.)$$

$$\text{NADH}_2 + \text{CHROMOGEN} \xrightleftharpoons{\text{Catalyst}} \text{CHROMOGEN} + \text{NAD} \quad (3.)$$
$$\text{(oxidized)} \qquad\qquad \text{(reduced)}$$

All enzymatic reactions listed above will follow this general scheme, where reaction (2.) is usually referred to as the coupling reaction, reactions (2.) or (3.) are the measuring reactions, and reaction (1.) may be characterized as the primary reaction. It is understood however, that not all three reactions are required for measurement; in fact, they may be limited to two, or one. In the case of the ultraviolet measurement of lactic dehydrogenase (LD) activity, only reaction (2.) is involved, as follows:

REACTION SCHEME 2.—LDH $$\text{Pyruvate} + \text{NADH}_2 \xrightleftharpoons{LDH} \text{NAD} + \text{Lactate}$$

Conversely, more than the three reactions listed may be involved as in the case of Creatine phosphokinase (CPK):

REACTION SCHEME 3.—CPK $$\text{CP} + \text{ADP} \xrightleftharpoons{CPK} \text{ATP} + \text{Creatine} \quad (1.)$$

$$\text{ATP} + \text{Glucose} \xrightarrow{HK} \text{Glucose-6-Phos.} + \text{ADP} \quad (2.)$$

$$\text{Glucose-6-Phos.} + \text{NAD} \xrightarrow{G\text{-6-PDH}} \text{NADH}_2 \quad (3.)$$

$$\text{NADH}_2 + (ox) \xrightleftharpoons{PMS} (red) + \text{NAD} \quad (4.)$$

SYMBOLS

CP = Creatine phosphate
ADP = Adenosine-5'-diphosphate
ATP = Adenosine triphosphate
HK = Hexokinase
NAD = nicotinamide-adenine dinucleotide
$NADH_2$ = nicotinamide-adenine dinucleotide, reduced
G-6-PDH = Glucose-6-phosphate dehydrogenase
INT = tetrazolium salt
PMS = phenazine methosulfate In this case, reactions (2.) and (3.) may be considered the coupling reactions, reactions (3.) or (4.) the measuring reactions, and reaction (1.) the primary reaction.

Referring to REACTION SCHEME 1,—GENERAL MODEL, it becomes obvious and is general knowledge that the use of the reaction sequence permits the analytical quantitation of either the reaction substrates/products or the catalyzing enzymes.

The quantitation of these constituents in biological fluids is a well accepted and widely used diagnostic tool in diagnosis and treatment of human and animal disease states.

Enzymes are large molecular weight, complex protein molecules, usually of unknown chemical structure. They are presently classified by their catalytic activity and extreme substrate specificity. Enzymes may be redefined as biological catalysts, capable of catalyzing a reaction of a single substrate, or a reaction of a similar group of substrates.

Coenzymes are lower molecular weight organic chemicals of well-defined structure, whose reactions or interactions are necessary for specific enzyme assay or reaction. They are catalyzed resulting in an irreversible change in the coenzyme's structure and/or atomic composition. Coenzymes are very useful in clinical assay procedure. Some have strong absorbance, their reactions are stoichiometric with the substrate and therefore the creation or disappearance of the absorbing form can be followed photometrically. Nicotinamide adenide dinucleotide (NAD) and its reduced form ($NADH_2$) are used in many important clinical assays such as the S.G.O.T., S.P.G.T. and LDH assays previously described. NAD and $NADH_2$ have a molecular weight of about 700 and are very complex organic molecules. $NADH_2$ absorbs strongly at 340 nm whereas NAD does not absorb at this wavelength.

$NADH_2$ is extremely unstable in water solution or in dry form when exposed to humid environments. Even when frozen $NADH_2$ must be kept free of moisture. Stability is better at alkaline pH, whereas at acid pH $NADH_2$ decomposes very rapidly in a matter of minutes. Neither the exact mechanism, nor the end products are of significance except that decomposed $NADH_2$ can no longer effectively function as a coenzyme nor does it possess the extinction coefficient at 340 nm. The typical commercial form is a dry dessicated package or freeze dried stored under nitrogen. $NADH_2$ is classically insoluble in organic solvents.

SUMMARY OF THE INVENTION

Labile coenzymes are treated according to the invention resulting in long term stability without affecting coenzymatic reactivity or photometric absorptivity. The invention provides reagents where quality control is assured throughout manufacturing, packaging, storage and use. The inconvenience of rigid package size is eliminated as is the high cost of packaging, freeze drying and reagent waste. Liquid enzyme and coenzyme systems provide application flexibility and separation of the ingredients is easily accomplished with negligible manufacturing cost providing the flexibility of triggering the desired reaction after all side reactions have been dissipated.

The stabilized coenzymes of the invention have been assessed in studies which compared liquid coenzyme reagents with fresh reagents. The studies show a 1:1 correlation between aged liquid and fresh reagents with comparable sensitivity and precision. Providing coenzyme reagents in a stable liquid form enhances the colorimetric applicability of present day NAD/NADH coupled methodologies primarily because the separation of ingredients is easily accomplished. Stable liquid reagents are especially advantageous where NADH consumption is the basis of measurement and the color reagent must be separated from NADH and the reaction main. In the ultraviolet mode, the liquid system offers better reagent homogeneity and packaging, as well as flexibility in usage, in contrast to the freeze-dried or dry media preparations.

In diagnostic enzymology, the stabilization of enzyme reagents in a ready-to-use liquid media is a new and exciting approach to satisfy the needs of the clinical laboratory and the reliability demands of the regulatory authorities. The flexibility of liquid enzyme systems insures their applicability to automated instrumentation, as well as their convenience in manual testings.

Stabilization of labile coenzymes is accomplished in accordance with the invention by dissolving the coenzymes in organic solvent. After solution is achieved at least 1% V/V of inert, hygroscopic solid is added and the container closed. The suspension is maintained at room temperature at least 1 hour, usually 1 to 2 days with occasional mixing to remove water from the mixture down to a level of no more than 0.05%. The solution may then be dispensed into amber-glass bottles containing at least 1% V/V hygroscopic agent which are sealed airtight and stored under refrigeration. Projected shelf life is up to 4 years under these conditions without appreciable degradation.

Surprisingly the coenzyme $NADH_2$ exhibits good solubility and stability in the aqueous miscible organic solvent even though solvents such as 1,2-propanediol are hygroscopic. Evidently the solvent molecules efficiently solvate the coenzyme protecting it from water and the solvent media acts as an efficient transfer media, delivering the absorbed water to the solid hygroscopic agent where it is irreversibly bound.

These and many other features and attendant advantages of the invention will become apparent as the invention becomes better understood by reference to the following detailed description.

DESCRIPTION OF THE PREFERRED EMBODIMENTS

The organic solvent should have the following characteristics:
1. Low water content (trace <0.1%);
2. Neutral or alkaline pH;
3. Liquid at room and refrigerator temperatures;
4. Does not react with $NADH_2$ other than forming electrostatic (i.e. hydrogen) bonds;
5. Miscible with water;
6. Standard free energy of solvolysis is low (normal resonance is established).

Non-reactive organic solvents of neutral or alkaline pH, such as alcohols especially liquid polyols containing from 2-4 hydroxyl groups and 2-10 carbon atoms are preferred, such as glycerol, ethylene glycol, propylene glycol or butane diol. Propylene glycol, 1,2-propanediol, was found to possess all these qualities and is the solvent of choice.

The inert hygroscopic solid maintains the desired low water content i.e. below 0.5% preferably below 0.1%. The hygroscopic solid must be an efficient water adsorber non-reactive with the coenzyme and of neutral or alkaline pH. The solid is preferably a high area hygroscopic agent such as a natural or synthetic molecular sieve having a particle size from 2-16 mesh present in an amount of at least 1% V/V typically from 5-20% V/V.

The amount of surface area is important since the material acts to adsorb water into the pores.

Molecular sieves are zeolites or similar materials whose atoms are arranged in a crystal lattice in such a way that there are a large number of small cavities interconnected by smaller openings or pores of precisely uniform size. Normally these cavities contain water molecules, but upon heating, this water is driven off without any change in the remaining crystal lattice. The network of cavities and pores may occupy 50% of the total volume of the crystals. Molecular sieves have a strong tendency to readsorb water.

A few natural zeolites exhibit molecular sieve characteristics to a limited degree. Synthetic zeolites are available in several sizes (pore openings 3, 4, 5 and 10 angstrom units in diameter) with high capacity for adsorption and regeneration even when used at elevated temperatures.

The coenzyme can be present up its solubility limit and is preferably as concentrated as possible since propylene glycol is a strong enzyme inhibitor and can interfere with the primary or coupling enzymatic activity if too much is carried into the test from the coenzyme reagent. Typical $NADH_2$ compositions according to the invention contain about 2–15 g/l typically about 7 g/l. Hydrated $NADH_2$ can be utilized for speedier solution in the polyol solvent. Example: 6.65 g/l of $NADH_2$ was dissolved in spectroquality 1,2-propanediol in a closed amber glass container. After complete solution is attained, 10% V/V of molecular sieves (4 mesh) were added and the container was closed and left at room temperature for 24 hours with occasional mixing to reduce water in the mixture below 0.01%. The solution was dispensed into final marketing amber-glass bottles containing fresh 4 mesh molecular sieves (10% v/v). The containers were sealed airtight and stored under refrigeration. An Arrhenius plot depicting the temperature stability profile of $NADH_2$ degradation in this media indicates storage stability of up to 4 years without significant degradation. The data was obtained at three storage temperatures of 60° C., room temperature (225° C.), and at refrigerated temperatures of 2°–8° C. (The mean of 4° C. was used.) The maximum allowable loss is less than 10% after 360 days storage at 27° C.

When propylene glycol is utilized without hygroscopic agent, $NADH_2$ degrades quite quickly in use when subject to opening and closing the container.

It is to be realized that only preferred embodiments of the invention have been described and that numerous substitutions, modifications and alterations are permissible without departing from the spirit and scope of the invention as defined in the following claims.

Having thus described the invention, what I desire to claim and secure by letters patent is:

1. A method of stabilizing a labile coenzyme used in biological diagnostic determinations and which coenzyme is normally unstable in aqueous media, said method comprising the steps of:
   dissolving the coenzyme in a non-reactive, water-miscible, organic solvent which is liquid at least at room temperatures to form a solution thereof, said coenzyme cooperating with and affecting reactivity of an enzyme in a biological diagnostic determination of a biological constitutent selected from the class consisting of:
   1. Glutamic-oxalacetic transaminase (SGOT);
   2. Glutamic-pyruvic transaminase (SGPT);
   3. Lactic dehydrogenase (LDH);
   4. Creatine Phosphokinase (CPK);
   5. a-Hydroxybuteric dehydrogenase (a-HBD);
   6. Glucose (via Hexokinase-G-6-PDH);
   adding at least 1% of an inert, high surface area, particulate, hygroscopic solid to the solution to form a suspension;
   stirring the suspension and entrapping water with the hygroscopic solid so that the residual water content is below 0.5% and where activity of the coenzyme remains unaffected by the presence of the organic solvent in the stabilized composition or in a biological diagnostic determination reaction; and
   sealing the suspension.

2. A method according to claim 1 in which the coenzyme is selected from $NADH_2$ or hydrated $NADH_2$.

3. A method according to claim 2 in which the concentration of $NADH_2$ is above 2 g/l.

4. A method according to claim 2 in which the solvent has the following characteristics:
   1. Low water content (trace <0.1%);
   2. Neutral or alkaline pH;
   3. Liquid at room and refrigerator temperatures;
   4. Does not react with $NADH_2$ other than forming electrostatic (i.e., hydrogen) bonds;
   5. Miscible with water;
   6. Standard free energy of solvolysis is low (normal resonance is established).

5. A method according to claim 4 in which the solvent is a polyol containing 2–4 hydroxyl groups and 2–10 carbon atoms.

6. A method according to claim 5 in which the solvent is a 1,2-propane diol.

7. A method according to claim 6 in which the suspension contains no more than 0.1% water before sealing.

8. A method according to claim 7 in which the inert hygroscopic solid is a molecular sieve present in an amount from 5–20% V/V.

9. A method according to claim 8 in which the molecular sieve has a particle size from about 2–16 mesh.

10. A stabilized liquid coenzyme composition used in biological diagnostic determinations and where said coenzyme affects the reactivity of an enzyme in such biological diagnostic determinations, said composition comprising a solution containing less than 0.1% water and comprising a labile coenzyme which is unstable in aqueous media, said coenzyme being dissolved in a non-reactive, water-miscible, organic solvent which is liquid at room and refrigerator temperatures containing at least 1% v/v of an inert, high surface area, particulate, solid hygroscopic agent, and where activity of the coenzyme reamins unaffected by the presence of the organic solvent in the stabilized composition or in a biological diagnostic determination reaction.

11. A composition according to claim 10 in which the coenzyme is selected from $NADH_2$ or hydrated $NADH_2$.

12. A composition according to claim 11 in which the concentration of $NADH_2$ is about 2 g/l.

13. A composition according to claim 10 in which the solvent is a polyol containing 2–4 hydroxyl groups and 2–10 carbon atoms.

14. A composition according to claim 13 in which the solvent is 1,2-propane diol.

15. A composition according to claim 14 in which the hygroscopic solid is a molecular sieve present in an amount from 5-20% v/v and having a particle size from 2-16 mesh.

16. A method of stabilizing a labile coenzyme used in biological diagnostic determinations and which coenzyme is normally unstable in aqueous media, said method comprising the steps of:

dissolving the coenzyme in a non-reactive, water-miscible organic solvent which is liquid at least at room temperatures to form a solution thereof, said coenzyme cooperating with and affecting reactivity of an enzyme in a biological diagnostic determination tion;

adding at least 1% of an inert, hygroscopic solid to the solution to form a suspension;

stirring the suspension and entrapping water with said hygroscopic solid so that the residual water content is below 0.5% and where activity of the coenzyme remains unaffected by the presence of the organic solvent in the stabilized composition or in a biological diagnostic determination reaction; and sealing the suspension.

17. A method according to claim 16 in which the coenzyme is selected from $NADH_2$ or hydrated $NADH_2$.

18. A method according to claim 17 in which the solvent has the following characteristics:
   1. Low water content (trace 0.1%);
   2. Neutral or alkaline pH;
   3. Liquid at room and refrigerator temperatures;
   4. Does not react with $NADH_2$ other than forming electrostatic (i.e., hydrogen) bonds;
   5. Miscible with water;
   6. Standard free energy of solvolysis is low (normal resonance is established).

19. A method according to claim 18 in which the solvent is a polyol containing 2-4 hydroxyl groups and 2-10 carbon atoms.

20. A method according to claim 19 in which the suspension contains no more than 0.1% water before sealing.

21. A method according to claim 20 in which the inert hygroscopic solid is a molecular sieve present in an amount from 5-20% V/V.

22. A method according to claim 21 in which the molecular sieve has a particle size from about 2-16 mesh.

23. A method of stabilizing a labile coenzyme used in biological diagnostic determinations and which coenzyme is normally unstable in aqueous media, said method comprising the steps of:

dissolving the coenzyme in a non-reactive water-miscible organic solvent which is liquid at least at room temperatures to form a solution thereof and so that the coenzyme is present in an amount at or near the limit of solubility, said coenzyme cooperating with and affecting reactivity of an enzyme in a biological diagnostic determination;

adding at least 1% of an inert, hygroscopic solid to the solution to form a suspension;

stirring the suspension and entrapping water with said hygroscopic solid so that the residual water content is below 0.5%, the activity of the coenzyme remaining unaffected by the presence of the organic solvent in the stabilized composition or in a biological diagnostic determination reaction; and sealing the suspension.

24. A method according to claim 23 in which the coenzyme is selected from $NADH_2$ or hydrated $NADH_2$.

25. A method according to claim 24 in which the concentration of $NADH_2$ is above 2 g/l.

26. A method according to claim 23 in which the solvent has the following characteristics:
   1. Low water content (trade >0.1%);
   2. Neutral or alkaline pH;
   3. Liquid at room and refrigerator temperatures;
   4. Does not react with $NADH_2$ other than forming electrostatic (i.e., hydrogen) bonds;
   5. Miscible with water;
   Standard free energy of solvolysis is low (normal resonance is established).

27. A method according to claim 26 in which the solvent is a polyol containing 2-4 hydroxyl groups and 2-10 carbon atoms.

28. A method according to claim 27 in which the solvent is a 1,2-propane diol.

29. A method according to claim 28 in which the suspension contains no more than 0.1% water before sealing.

30. A method according to claim 29 in which the inert hygroscopic solid is a molecular sieve present in an amount from 2-20% v/v.

31. A method according to claim 30 in which the molecular sieve has a particle size from about 2-16 mesh.

32. A stabilized liquid coenzyme composition used in biological diagnostic determinations and where said coenzyme affects the reactivity of an enzyme in such biological diagnostic determinations, said composition comprising a labile coenzyme which is unstable in aqueous media, said coenzyme being dissolved in a non-reactive, water-miscible, organic solvent which is liquid at room and refrigerator temperatures containing at least 1% V/V of an inert, solid hygroscopic agent such that the water content is less than 0.5%, and where activity of the coenzyme remains unaffected by the presence of the organic solvent in the stabilized composition or in a biological diagnostic determination reaction.

33. A composition according to claim 32 in which the coenzyme is selected from $NADH_2$ or hydrated $NADH_2$.

34. A composition according to claim 33 in which the concentration of $NADH_2$ is above 2g/l.

35. A composition according to claim 32 in which the solvent is a polyol containing 2-4 hydroxyl groups and 2-10 carbon atoms.

36. A composition according to claim 35 in which the solvent is 1,2-propane diol.

37. A composition according to claim 36 in which the hygroscopic solid is a molecular sieve present in an amount from 5-20% v/v and having a particle size from 2-16 mesh.

38. A method of stabilizing a labile coenzyme used in biological diagnostic determinations and which coenzyme is normally unstable in aqueous media, said method comprising the steps of:

dissolving the coenzyme in a non-reactive, water-miscible, polyol which is liquid at room and refrigerator temperatures to form a solution thereof, said coenzyme cooperating with and affecting reactivity of an enzyme in a biological diagnostic determination;

said polyol containing 2–4 hydroxyl groups and 2–10 carbon atoms and having the following characteristics:
1. Low water content (trace 0.1%),
2. Neutral or alkaline pH,
3. Liquid at room and refrigerator temperatures,
4. Does not react with the coenzyme other than forming electrostatic (i.e., hydrogen) bonds,
5. Miscible with water,
6. Standard free energy of solvolysis is low (normal resonance is established;

adding at least 1% of an inert, high surface area, particulate, hygroscopic solid to the polyol soution to form a suspension;

stirring the suspension and entrapping water with said hygroscopic solid so that the residual water content is below 0.5% and where activity of the coenzyme remains unaffected by the presence of the polyol in the stabilized composition or in a biological diagnostic determination reaction; and sealing the suspension.

39. A method according to claim 38 in which the coenzyme is selected from $NADH_2$ or hydrated $NADH_2$.

40. A method according to claim 39 in which the concentration of $NADH_2$ is above 2g/l.

41. A method according to claim 40 in which the solvent is a 1,2-propane diol.

42. A method according to claim 41 in which the inert hygroscopic solid is a molecular sieve present in an amount from 5–20% V/V and has a particle size from about 2–16 mesh.

43. A method according to claim 42 in which the suspension contains no more than 0.1% water before sealing.

* * * * *